US010286096B2

(12) United States Patent
Casonato

(10) Patent No.: US 10,286,096 B2
(45) Date of Patent: May 14, 2019

(54) DEVICE FOR DISCHARGING LOOSE PRODUCTS FROM A TREATMENT MACHINE

(71) Applicant: ICOS PHARMA S.P.A., Zoppolo (IT)

(72) Inventor: Ottorino Casonato, Castelfranco Veneto (IT)

(73) Assignee: ICOS PHARMA S.P.A., Zappola (IT)

( * ) Notice: Subject to any disclaimer, the term of this patent is extended or adjusted under 35 U.S.C. 154(b) by 81 days.

(21) Appl. No.: 15/514,391

(22) PCT Filed: Sep. 24, 2015

(86) PCT No.: PCT/IB2015/057355
§ 371 (c)(1),
(2) Date: Mar. 24, 2017

(87) PCT Pub. No.: WO2016/046781
PCT Pub. Date: Mar. 31, 2016

(65) Prior Publication Data
US 2017/0290939 A1    Oct. 12, 2017

(30) Foreign Application Priority Data
Sep. 24, 2014  (IT) ............................. UD2014A0154

(51) Int. Cl.
*A61L 2/26*         (2006.01)
*B65B 37/14*        (2006.01)
(Continued)

(52) U.S. Cl.
CPC ...... *A61L 2/26* (2013.01); *B08B 3/10* (2013.01); *B08B 5/02* (2013.01); *B08B 9/00* (2013.01);
(Continued)

(58) Field of Classification Search
CPC .... A61L 2/26; B08B 9/00; B08B 5/02; B08B 5/023; B08B 3/10; B65B 55/02; B65B 55/12; B65B 37/14; B65B 2210/10
See application file for complete search history.

(56) References Cited

U.S. PATENT DOCUMENTS

| 5,447,699 A | 9/1995 | Papciak et al. |
| 6,659,115 B1 | 12/2003 | Wieczorek |
| 2012/0000161 A1* | 1/2012 | Free .......................... B65B 1/46 53/113 |

FOREIGN PATENT DOCUMENTS

| EP | 1 640 647 A2 | 3/2006 |
| JP | 2013-094768 A | 5/2013 |

OTHER PUBLICATIONS

International Search Report and Written Opinion for PCT/IB2015/057355, dated Jan. 28, 2016.

* cited by examiner

*Primary Examiner* — Timothy C Cleveland
(74) *Attorney, Agent, or Firm* — Marshall, Gerstein & Borun LLP

(57) ABSTRACT

Device for discharging loose products includes a conveyor body attachable with its first end to a treatment machine for the loose products. The conveyor body, in correspondence to its second end, comprises a wall in which a collection aperture is made, selectively openable/closable by means of an opening/closing member to allow the discharge of said loose products. The discharge device for loose products further includes a pneumatic deliverer located in the conveyor body and configured to deliver a stream of gas at least toward the wall and determine the discharge, through the collection aperture, at least of the loose products that are deposited on the wall.

12 Claims, 3 Drawing Sheets

(51) Int. Cl.
- *B65B 55/02* (2006.01)
- *B08B 3/10* (2006.01)
- *B08B 5/02* (2006.01)
- *B08B 9/00* (2006.01)
- *B01L 1/02* (2006.01)

(52) U.S. Cl.
CPC .............. *B65B 37/14* (2013.01); *B65B 55/02* (2013.01); *B01L 1/02* (2013.01); *B65B 2210/10* (2013.01)

DEVICE FOR DISCHARGING LOOSE PRODUCTS FROM A TREATMENT MACHINE

FIELD OF THE INVENTION

The present invention concerns a device to selectively discharge loose products from a treatment machine, such as a sterilizing machine, a washing machine or suchlike.

In particular, the device according to the present invention can be used to discharge loose products such as, merely by way of non-restrictive example, closing stoppers of test tubes for laboratory analyses, or small instruments or objects used in operating theatres or laboratories.

The present invention also concerns a treatment machine that comprises a device for discharging loose products.

BACKGROUND OF THE INVENTION

Machines for treating loose products are known, for example to perform sterilization or washing treatments on closing stoppers of test tubes for laboratory analyses, small instruments or objects used in operating theatres or laboratories.

Within the field of sterilization, it is known to sterilize the loose products in sterilization machines provided with an airtight chamber in which a rotary drum receives the products to be sterilized on a loading side, or "dirty" side; it then sterilizes the products during a treatment cycle that normally lasts between one and five hours, and then discharges them on a discharge side or "sterile" side, so they can be packaged.

The rotary drums are typically divided up into sectors, or baskets, each containing a predefined quantity of loose products to be loaded into packages after sterilization.

The discharge operations provide to position one of the sectors on each occasion in proximity to a discharge aperture provided in correspondence with the discharge side of the airtight chamber, and then to discharge the loose products present in the sector.

A conveyor body is typically attached to the discharge aperture with a first end; the conveyor body defines a conveyor compartment to direct the loose products that are discharged from the baskets toward the package where they are collected.

The conveyor body is provided with a second end, opposite the first end, having a collection aperture in correspondence with which the package is attached in order to collect the loose products.

The collection aperture is usually made in a plate or wall positioned to close the conveyor compartment.

The conveyor body is also provided with an opening/closing member, configured to selectively open or close the collection aperture. The opening/closing member guarantees the airtight seal of the chamber during the sterilization process, and allows to discharge the loose products from the chamber once the sterilization process is terminated.

One disadvantage of this known solution is that during the discharge operations some loose products can position themselves stably in dead zones of the conveyor compartment, for example in correspondence with the plate where there is the collection aperture.

This does not guarantee that the predefined number of loose products will be present in the package, and therefore it does not guarantee a precise metering of the loose products into the package.

In some situations, moreover, the loose products can be positioned in correspondence with the edges defining the collection aperture, and can interfere for example with the closing of the opening/closing member.

In the latter case, intervention is often required by operators, to remove and evacuate the loose products from the conveyor body. However, these interventions entail a loss of the sterile conditions of the chamber, and therefore another sterilization cycle is required to sterilize the loose products in the chamber.

Within the field of transferring loose products pneumatic transporters are also known, used in plants for washing stoppers, an example of which is described in JP-A-2013.94768.

Pneumatic transporters of this type comprise a tubular element, hollow inside and through which the stoppers are made to pass.

The tubular element comprises a plurality of delivery nozzles disposed both longitudinally and angularly distanced along the development of the tubular element.

In particular, the delivery nozzles have delivery apertures disposed inside the tubular element, each of which delivers a stream of gas in a longitudinal direction of the tubular element.

The streams of gas delivered in the tubular element determine a thrust of the stoppers in a longitudinal direction along the tubular element itself.

However, this solution is not able to solve the problem of the unwanted positioning of loose products in dead zones of the tubular element, and therefore is not able to ensure the correct transfer of all the loose products to the desired destination.

There is therefore a need to perfect a device for discharging loose products for a treatment machine that can overcome at least one of the disadvantages of the state of the art.

In particular, one purpose of the present invention is to obtain a device for discharging loose products for a treatment machine that allows correct operations to discharge the loose products from the treatment machine.

Another purpose of the present invention is to obtain a device for discharging loose products that is reliable and accurate.

Another purpose of the present invention is to obtain a device for discharging loose products that limits, and even eliminates, control and maintenance interventions by operators.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purposes, a device for discharging loose products comprises a tubular conveyor body defined by at least one perimeter wall and provided with a first end attachable to a treatment machine for the loose products, a second end opposite the first end, and a bottom wall attached in correspondence to the second end and disposed transversely to the perimeter wall to partly occlude the tubular transit section of the conveyor body.

A collection aperture is made in the bottom wall, selectively openable/closable by means of an opening/closing member to allow the discharge of the loose products.

According to one aspect of the present invention, the device comprises a delivery nozzle located in the conveyor body, with at least one delivery aperture that faces toward the bottom wall and is configured to deliver a stream of gas incident against the bottom wall to determine the discharge, through the collection aperture, at least of the loose products that are deposited on the bottom wall.

In this way, possible loose products that are deposited during discharge on the bottom wall can be displaced by the stream of gas in order to convey them toward the collection aperture. This allows to guarantee that all the loose products, which are usually loaded in individual containers present in the treatment chamber, are discharged, ensuring that the packages have the predefined number of loose products.

The stream of gas also prevents possible loose products from depositing in correspondence with the collection aperture, constituting an obstacle for the closing of the opening/closing member.

The presence of delivery nozzles also avoids positioning, even in a mobile manner, any parts such as discharge hoppers or funnels, directly in correspondence with the collection aperture that not only might interfere with the opening and closing movements of the opening/closing member, but also do not allow to maintain the sterile conditions of the loose products.

Some forms of embodiment of the present invention also concern a method for discharging loose products from a treatment machine, which provides to make the loose products pass through a conveyor body of a discharge device attached with a first end to the treatment machine, having at least one perimeter wall and provided, in correspondence with its second end opposite the first end, with a bottom wall disposed transversely to the perimeter wall to partly occlude the tubular transit section of the conveyor body.

The method also provides to discharge the loose products through a collection aperture, selectively openable/closable by an opening/closing member, and provided in the bottom wall.

According to a possible implementation, the method comprises the emission, with a delivery nozzle, of a stream of gas incident against the bottom wall to determine the discharge, through the collection aperture, at least of the loose products that are deposited on the bottom wall.

These and other aspects, characteristics and advantages of the present disclosure will be better understood with reference to the following description, drawings and attached claims. The drawings, which are integrated and form part of the present description, show some forms of embodiment of the present invention, and together with the description, are intended to describe the principles of the disclosure.

The various aspects and characteristics described in the present description can be applied individually where possible. These individual aspects, for example aspects and characteristics described in the attached dependent claims, can be the object of divisional applications.

It is understood that any aspect or characteristic that is discovered, during the patenting process, to be already known, shall not be claimed and shall be the object of a disclaimer.

BRIEF DESCRIPTION OF THE DRAWINGS

These and other characteristics of the present invention will become apparent from the following description of some forms of embodiment, given as a non-restrictive example with reference to the attached drawings wherein.

Figure 1:
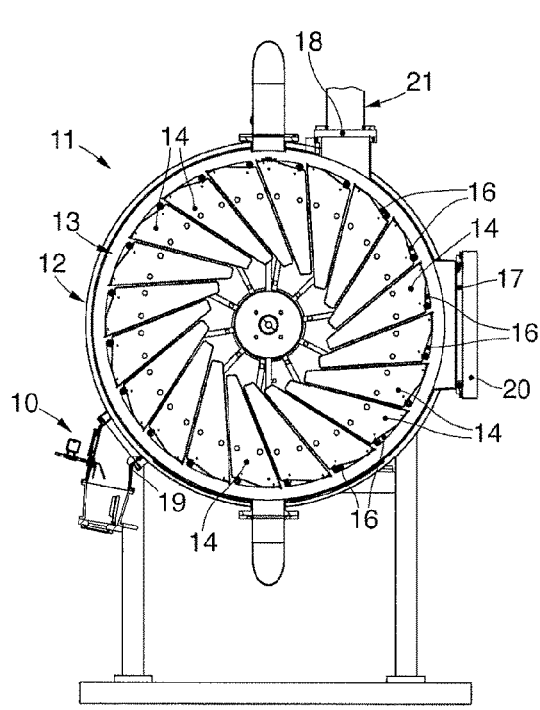
FIG. 1 is a lateral section view of a treatment machine provided with a device for discharging loose products according to a possible form of embodiment of the present invention.
Figure 4:
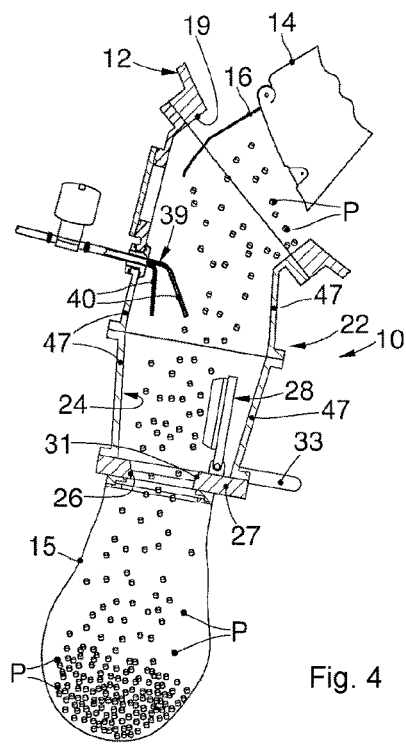
FIG. 4 is a partial enlarged view of FIG. 2 in a first operating condition.

To facilitate comprehension, the same reference numbers have been used, where possible, to identify identical common elements in the drawings. It is understood that elements and characteristics of one form of embodiment can conveniently be incorporated into other forms of embodiment without further clarifications.

DETAILED DESCRIPTION OF SOME FORMS OF EMBODIMENT

We shall now refer in detail to the various forms of embodiment of the present invention, of which one or more examples are shown in the attached drawings. Each example is supplied by way of illustration of the invention and shall not be understood as a limitation thereof. For example, the characteristics shown or described insomuch as they are part of one form of embodiment can be adopted on, or in association with, other forms of embodiment to produce another form of embodiment. It is understood that the present invention shall include all such modifications and variants.

Before describing these forms of embodiment, we must also clarify that the present description is not limited in its application to details of the construction and disposition of the components as described in the following description using the attached drawings. The present description can provide other forms of embodiment and can be obtained or executed in various other ways. We must also clarify that the phraseology and terminology used here is for the purposes of description only, and cannot be considered as limitative.

With reference to FIG. 1, a device for discharging loose products P is indicated in its entirety by the reference number 10 and can be installed on a treatment machine 11 in which the loose products P are loaded to be subjected to treatment, for example sterilization, washing, ultrasound or other.

Hereafter in the description we shall describe a treatment machine 11 to sterilize the loose products P, although it is not excluded that the treatment machine 11 can possibly be applied for other treatments.

According to the form of embodiment in FIG. 1, the treatment machine 11 comprises a treatment chamber 12 into which the loose products P are introduced, manually or automatically, to be sterilized.

A rotary drum 13 is installed in the treatment chamber 12 and supports a plurality of containers 14 or baskets, conventionally from four to twenty-four, in FIG. 1 by way of example twenty.

Into each of the containers 14 a predefined number of loose products P are introduced, substantially coinciding with the predefined number of loose products P that have to be packaged in a package 15, shown schematically in FIGS. 2-6.

Each container 14 can be shaped like a pyramid, a truncated pyramid, or conical or truncated cone, and can occupy a predefined angular sector of the rotary drum 13.

The volume of the container 14 determines the metered quantity of loose products P that can be contained.

Each container 14 can include a door 16 that can be selectively opened or closed, to allow the introduction or removal of the loose products P into or from it.

Each container 14 can include an opening device, not visible in the drawings, which is connected to the door 16 to move it from the closed to the open position and vice versa, and in this way to allow the operations to load/unload the loose products P and also the treatments in the treatment chamber 12. The opening device can comprise an actuator, a motor, levers or mechanical kinematisms configured to selectively open/close the door 16 in an automated manner.

The treatment chamber 12 is provided with an aperture 17 to allow access to the treatment chamber 12. The aperture 17 can be provided with a door 20, able to be selectively opened/closed, to allow access to the treatment chamber 12, for example to manually load the loose products P to be sterilized, or to carry out possible maintenance operations.

The treatment chamber 12 can also or alternatively comprise an automated loading aperture 18 to load the loose products P into the containers 14.

The automated loading aperture 18 can be connected, in turn, to an apparatus 21 to feed the loose products P, only partly shown in FIG. 1 and which is configured to feed, possibly also metering them, the loose products P into the containers 14.

The treatment chamber 12 also comprises a discharge aperture 19 through which the loose products P can be discharged from the containers 14 once treatment has been carried out.

The rotary drum 13 can be selectively rotated around its axis of rotation both to allow the treatment to be carried out, and also to position on each occasion one of the containers 14 in correspondence with the aperture 17, the automated loading aperture 18 or again the discharge aperture 19, to allow loading or unloading of the loose products P into or from the container 14.

The discharge device 10 is attached in correspondence with the discharge aperture 19, to allow the transfer of the loose products P from the treatment chamber 12 to the package 15.

Figure 2:
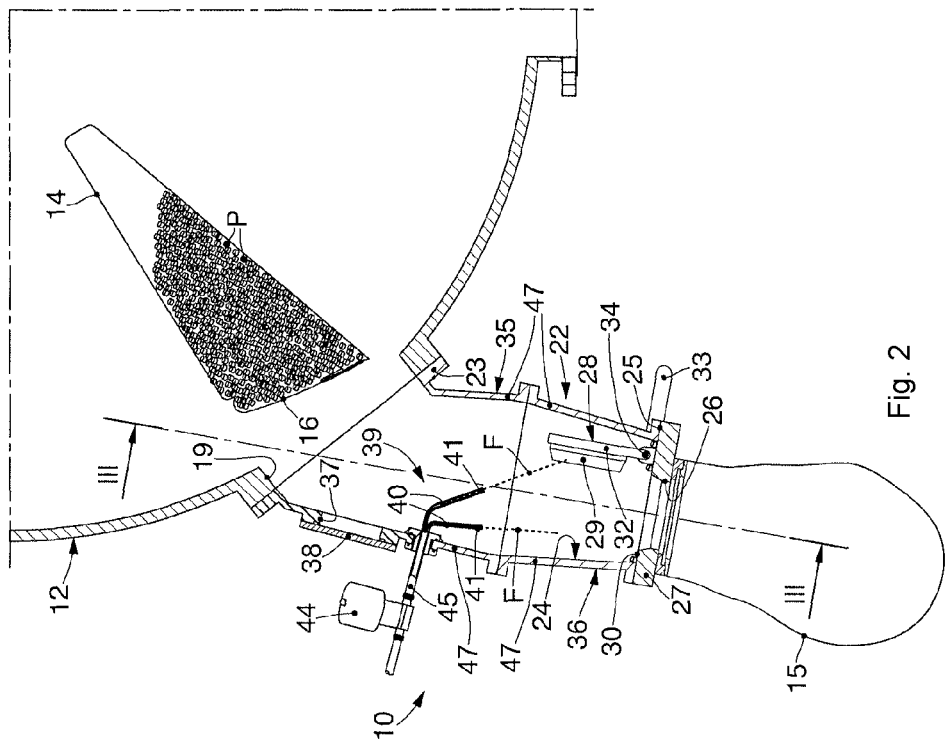
FIG. 2 is a section view of a device for discharging loose products according to a possible form of embodiment.
Figure 3:
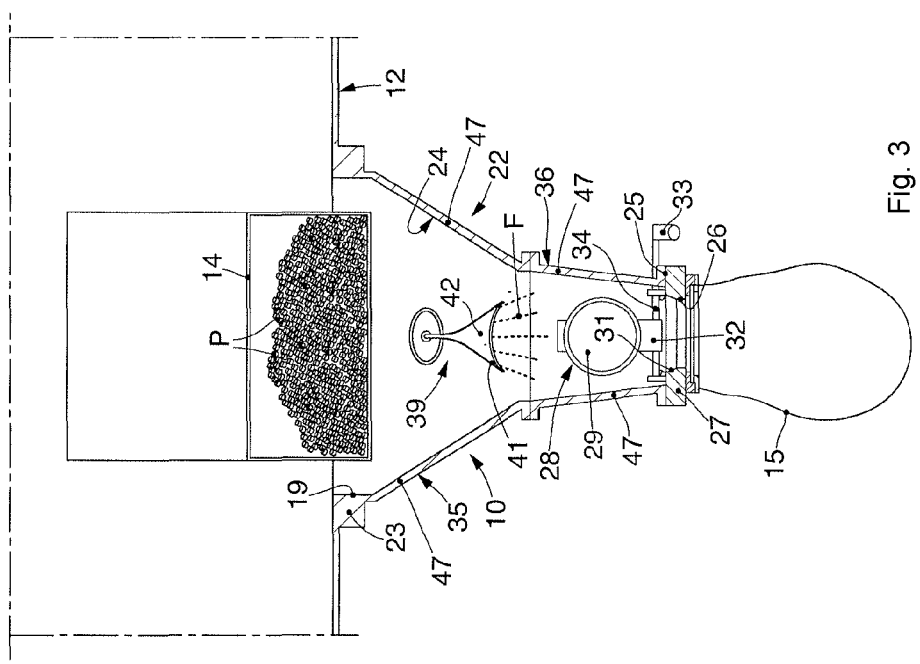
FIG. 3 is a section view from III to III in FIG. 2 and according to another form of embodiment.

According to FIGS. 2 and 3, a possible form of embodiment is described of the discharge device 10 according to the present invention.

The discharge device 10 comprises a conveyor body 22 attached during use with a first end 23 to the treatment chamber 12 in correspondence with the discharge aperture 19.

The conveyor body 22 is defined by at least one perimeter wall 47, in the case shown here a plurality of perimeter walls 47 suitably connected to each other to define a tubular conformation of the conveyor body 22. The tubular conformation of the conveyor body 22 allows to obtain a peripherally closed cross section, so as to maintain the sterility of the loose products P following treatment.

In correspondence with a second end 25, opposite the first end 23, the conveyor body 22 comprises a bottom wall 27 disposed transverse to the perimeter walls 47 so as to partly occlude the tubular transit section of the conveyor body 22.

A collection aperture 26 is also made in the bottom wall 27, through which the loose products P arriving from the treatment chamber 12 are discharged.

The collection aperture 26 for the passage of the loose products P is smaller in size than the section of the conveyor body 22, evaluated at least in correspondence with the second end 25 of the latter.

According to a possible solution, the package 15 used to collect the loose products P exiting from the treatment chamber 12 can be selectively attached in correspondence with the collection aperture 26.

The collection aperture 26 can be provided with suitable attachment and fastening means to attach the package 15, suitable to allow the selective attachment and connection thereof.

The conveyor body 22 defines a conveyor compartment 24 communicating during use with the inside of the treatment chamber 12, and which allows to convey the loose products P in a controlled manner toward the collection aperture 26.

The collection aperture 26 can be made in the thickness of the bottom wall 27.

In particular, the bottom wall 27 has a surface portion 30 (FIG. 2) that defines the transverse closing of the conveyor compartment 24 and perimeter edges 31 that define the development of the collection aperture 26.

The surface portion 30 can be substantially flat, and can be disposed substantially orthogonal to the perimeter walls 47 that define the conveyor body 22.

The conveyor body 22 also comprises an opening/closing member 28 configured to selectively open or close the collection aperture 26.

In particular, the opening/closing member 28 is kept in position to close the collection aperture 26 at least during the operations to treat the loose products P, and is opened to allow them to be discharged.

According to a possible solution, the opening/closing member 28 is located inside the conveyor compartment 24, in order to maintain the sterile or at least clean conditions.

The opening/closing member 28 can comprise at least one stopper element 29, having a shape substantially mating with that of the collection aperture 26 and which, during use, is selectively disposed to obstruct the collection aperture 26.

The opening/closing member 28 can also comprise a support arm 32, having a first end to which the stopper element 29 is attached, and a second end to which an actuation element 33 is connected.

The actuation element 33 can be selectively activated manually or automatically, to take the stopper element 29 to the position where it obstructs the collection aperture 26 or opens it.

The actuation element 33 can be chosen from a group comprising a lever, a kinematic mechanism, an actuator, a motor or a possible combination thereof.

According to the solution shown in FIGS. 2 and 3, the support arm 32 is pivoted in the conveyor body 22 and by rotating it around the pivoting axis it is possible to take the stopper element 29 to a condition where the collection aperture 26 is open or closed.

In particular, according to a possible solution, the second end of the support arm 32 is pivoted around a pin 34 and the actuation element 33 is configured to make the support arm 32 rotate around the pin 34 and to make the stopper element 29 assume the positions to obstruct or open the collection aperture 26.

The pin 34 can be attached to at least one of the perimeter walls 47 that define the conveyor body 22, or can be attached to the bottom wall 27.

According to one form of embodiment of the invention, the discharge device 10 comprises a pneumatic deliverer 39 located in the conveyor body 22 and configured to deliver a stream of gas F toward the bottom wall 27.

The stream of gas F is able to generate turbulence in the conveyor compartment 24, such as to displace the loose products P that have been deposited in dead zones of the conveyor body 22, for example in the space comprised between the rotation pin 34 of the opening/closing member 28 and the bottom wall 27.

According to a possible solution, the pneumatic deliverer 39 can comprise one or more delivery nozzles 40, located in the conveyor compartment 24 and each having its own delivery aperture 41 to deliver the stream of gas F, which faces toward the bottom wall 27.

In this way the stream of gas F has a field of action substantially incident against the bottom wall 27 which generates turbulence in the second end 25 of the conveyor compartment 24, so as to discharge the loose products P.

The number of delivery nozzles 40 can be chosen according to the sizes of the bottom wall 27, and so that the combined streams of gas F generated substantially strike the whole bottom wall 27.

According to a possible solution, at least one of the delivery nozzles 40, in FIG. 2 the delivery nozzle 40 on the left, is installed in the conveyor body 22 so as to dispose its delivery aperture 41 facing toward the collection aperture 26. In this way possible loose products P that are deposited near the collection aperture 26, for example on the perimeter edges 31, can be discharged, preventing interference with the closing of the opening/closing member 28.

Figure 7:
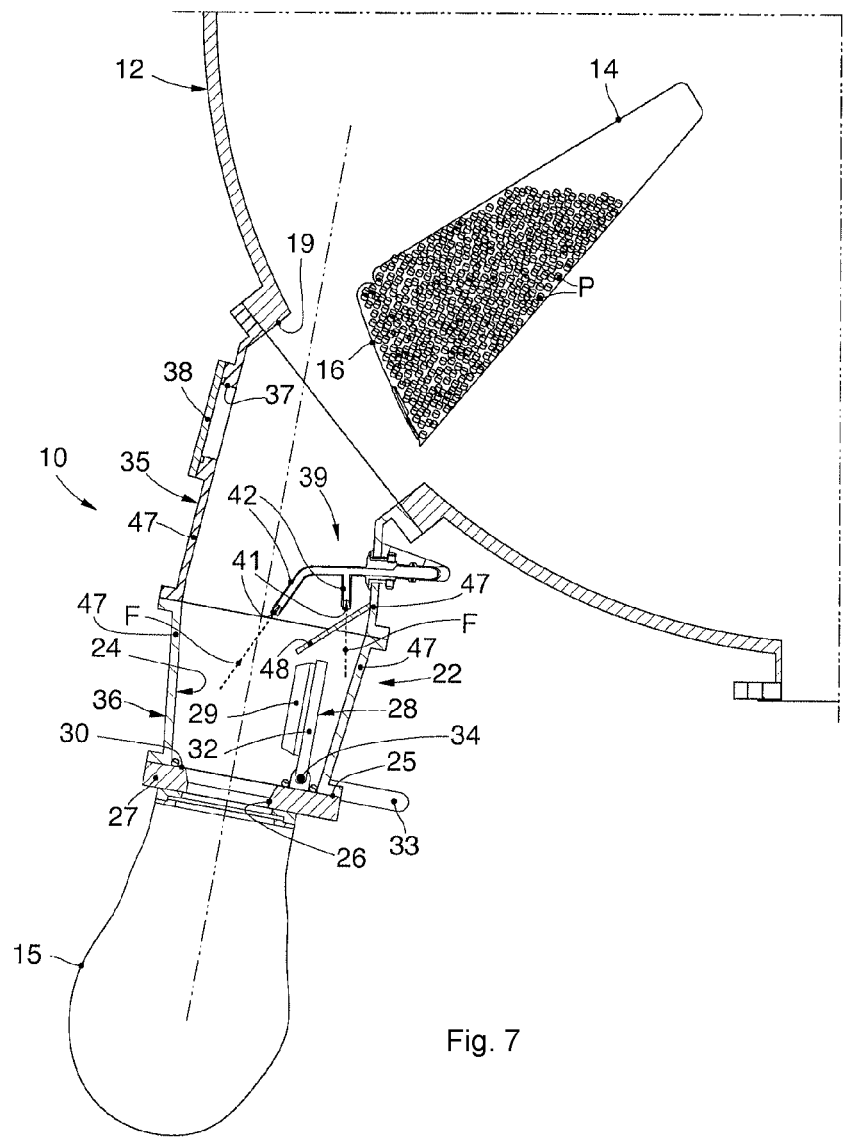
FIG. 7 shows a possible variant form of embodiment of FIG. 2.

According to a variant, shown for example in FIG. 7, at least one delivery nozzle 40 is positioned so as to dispose its delivery aperture 41 facing toward the connection zone of the support arm 32 to the conveyor body 22.

The connection zone can in fact constitute a temporary deposit zone for the loose products P, and the delivery of the stream of gas F prevents such deposit.

The delivery nozzles 40, or at least some of them, can be associated or integrated with orientable elements, for example articulations, joints, hinges or flexible tubes, configured to define a predefined positioning and orientation of the delivery aperture 41 in the conveyor compartment 24.

According to a possible variant shown in FIG. 3 and possibly combinable with the forms of embodiment described here, the delivery nozzle 40 comprises a nozzle with an air blade 42, having its delivery aperture 41 configured as a slit, facing during use toward the bottom wall 27 and configured to emit a stream of gas F of the laminar type that at least partly surrounds the collection aperture 26.

The laminar stream of gas F generates, in the conveyor compartment 24, a blade of air that conveys the loose products P directly toward the collection aperture 26, preventing them from depositing on the bottom wall 27.

According to possible forms of embodiment, the pneumatic deliverer 39 is attached to at least one of the perimeter walls 47 of the conveyor body 22.

According to possible implementations, the delivery nozzle 40 is located above the opening/closing member 28, to guarantee that all the loose products P are discharged and to prevent the delivery nozzle 40 from interfering with the movements of the opening/closing member 28.

The delivery nozzle 40 can be connected to a gas feed unit, not shown in the drawings, configured to supply gas under pressure to the delivery nozzle 40.

The gas feed unit can also be provided with sterilization devices suitable to sterilize gas and feed it to the delivery nozzle 40. This allows to guarantee sterility in the transfer and discharge of the loose products P to the package 15.

According to possible forms of embodiment, a stream of gas, chosen from a group comprising air, carbon dioxide, oxygen or other gases suitable for the purpose, is delivered through the pneumatic deliverer 39 or the delivery nozzle 40.

The pneumatic deliverer 39 can comprise a feed pipe 45 fixed through at least one of the perimeter walls 47 of the conveyor body 22 and suitable sealing means can be provided, to guarantee the sterility of the conveyor compartment 24.

The pneumatic deliverer 39 can also comprise a pressure regulator 44, configured to regulate the pressure at which the stream of gas F is delivered.

According to a possible solution, the conveyor body 22 can comprise at least one tubular element attached with a first end 23 to the treatment chamber 12.

The conveyor body 22 can be attached to the treatment chamber 12 by removable mechanical connections, for example threaded connections, pins or suchlike.

To this purpose, the first end 23 of the conveyor body 22 can be provided with a connection flange to allow selective connection to the treatment chamber 12. The connection flange allows a rapid installation, replacement and adaptability of the conveyor body 22 to the treatment chamber 12.

According to the forms of embodiment in FIGS. 2-7, the conveyor body 22 comprises a first tubular element 35 and a second tubular element 36 reciprocally connected in succession to each other.

The first tubular element 35 is attached to the treatment chamber 12, for example by the flange, or non-removably, for example by welding.

The first tubular element 35 can have a substantially conical shape, truncated cone, pyramid or truncated pyramid with the bigger section attached to the treatment chamber 12.

This section shape allows to define a conveying action and collection of the loose products P when they are discharged.

The pneumatic deliverer 39 or the delivery nozzle 40 can be attached on the wall of the first tubular element 35.

The bottom wall 27 is attached to the second tubular element 36, which is connected in succession with the first tubular element 35.

The second tubular element 36 can have a substantially cylindrical shape, or conical, pyramid, truncated pyramid or parallelepiped.

According to the form of embodiment in FIGS. 2 and 3, the second tubular element 36 has a parallelepiped shape with a rectangular base.

The second tubular element 36 has sizes suitable to contain inside it the opening/closing member 28, and to allow it to be moved, for example for the passage from the open to the closed position.

According to a possible solution, the conveyor body 22 can be provided with an inspection aperture 37, to allow to inspect the conveyor compartment 24.

According to a possible form of embodiment, shown for example in FIGS. 2-6, the inspection aperture 37 can be made in the first tubular element 35.

The inspection aperture 37 can be selectively opened/closed by a closing lid 38 attached to the perimeter wall 47 of the conveyor body 22.

Figure 6:
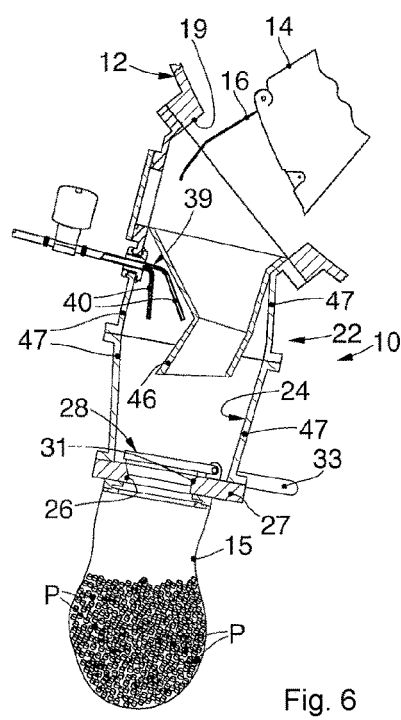
FIG. 6 is a partial enlarged view of FIG. 2 in a third operating condition.

According to a possible form of embodiment, shown in FIG. 6, the conveyor body 22 can comprise a conveyor element 46, conformed as a funnel or a hopper, and installed, with its larger cross section, in correspondence with the first end 23 of the conveyor body 22. The smaller cross section is instead disposed facing toward the collection aperture 26. The conveyor element 46 therefore supplies an aid to the pneumatic deliverer 39, to prevent loose products P from depositing on the bottom wall 27.

According to possible solutions, the conveyor element 46 can be provided, at least on the surface suitable to receive the loose products P during use, with surface irregularities, such as grooves, holes or ribs, configured to promote the outflow of the loose products P when they are discharged from the treatment chamber 12.

According to a preferential solution, the conveyor element 46 is provided with a plurality of through holes made in the walls that define the conveyor element 46, having smaller sizes than those of the loose products P to be transferred, and suitable to prevent the temporary depositing of the latter.

According to another form of embodiment of the present invention, one or more diverters 48 can be installed in the conveyor body 22, configured to divert the flow of loose products P during their transit through the conveyor body 22.

The diverter 48 can be conformed as a plate and can be attached to the conveyor body 22 in a transverse direction with respect to the perimeter walls 47.

The diverter 48 can be disposed above the opening/closing member 28, when the latter is in the open condition, to cover at least the pivoting zone of the opening/closing member 28 to the conveyor body 22.

The diverter 48 diverts the loose products P and prevents them from depositing in zones that are difficult to access, such as, precisely, the pivoting zone of the opening/closing member 28.

With reference to FIGS. 2-6 we shall now describe the steps of discharging loose products P from the treatment machine 11.

In particular, once the treatment cycle of the loose products P has been terminated, one of the containers 14 is moved in correspondence with the discharge aperture 19 of the treatment chamber 12 (FIGS. 2 and 3).

A package 15 is attached to the collection aperture 26, to collect the loose products P that will be discharged.

The opening/closing member 28 is activated to open the collection aperture 26.

In this condition, the door 16 of the container 14 (FIG. 4) is commanded to open, so that the loose products P as they exit pass through the conveyor compartment 24 and are collected in the package 15.

Figure 5:
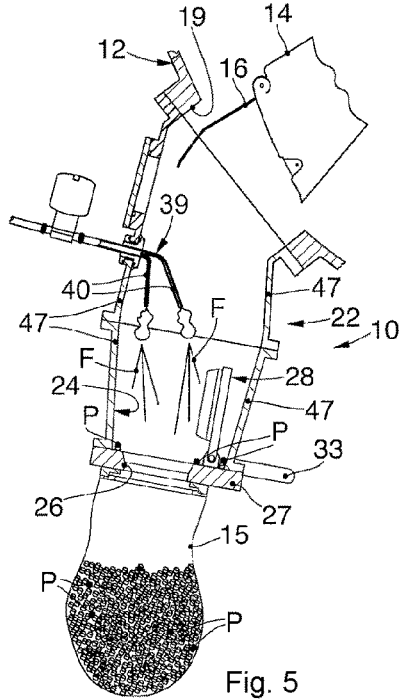
FIG. 5 is a partial enlarged view of FIG. 2 in a second operating condition.

During the discharge, some loose products P can deposit on the bottom wall 27 as shown in FIG. 5.

The delivery nozzle 40 is activated to move at least the loose products P that are deposited on the bottom wall 27 and to direct them toward the collection aperture 26. The delivery nozzle 40 can be activated before, at the same time as or immediately after the opening of the door 16 of the container 14.

The delivery nozzle 40 can be kept active for a determinate period of time after the opening of the door 16, so as to ensure the loose products P are completely discharged.

Then the collection aperture 26 is closed (FIG. 6) and the package 15 is subsequently removed.

It is clear that modifications and/or additions of parts may be made to the discharge device 10 as described heretofore, without departing from the field and scope of the present invention.

It is also clear that, although the present invention has been described with reference to some specific examples, a person of skill in the art shall certainly be able to achieve many other equivalent forms of discharge device, having the characteristics as set forth in the claims and hence all coming within the field of protection defined thereby.

The invention claimed is:

1. A device for discharging loose products, comprising: a tubular conveyor body defined by at least one perimeter wall and provided with a first end attachable to a treatment machine for said loose products, with a second end opposite the first end, and with a bottom wall attached in correspondence to said second end and disposed transversely to said perimeter wall to partly occlude a tubular transit section of said conveyor body, a collection aperture being made in said bottom wall, selectively openable/closable by means of an opening/closing member to allow the discharge of said loose products, and further comprising at least one delivery nozzle located in said conveyor body, having at least one delivery aperture that faces at least toward said bottom wall and is configured to deliver a stream of gas incident against said bottom wall to determine the discharge, through said collection aperture, at least of the loose products that are deposited on said bottom wall.

2. The device as in claim 1, wherein said collection aperture has a passage size of the loose products smaller than the tubular transit section of the conveyor body, evaluated at least in correspondence to said second end.

3. The device as in claim 1, wherein said at least one delivery aperture of said at least one delivery nozzle faces toward the collection aperture.

4. The device as in claim 1, wherein said at least one delivery nozzle comprises a nozzle with a blade of air having the at least one delivery aperture configured as a slit, facing during use toward said bottom wall and configured to emit a stream of gas of the laminar type that at least partly surrounds said collection aperture.

5. The device as in claim 1, wherein said opening/closing member is located in said conveyor body and in that said at least one delivery nozzle is located above said opening/closing member.

6. The device as in claim 5, wherein said opening/closing member is attached to said bottom wall.

7. The device as in claim 6, wherein said opening/closing member comprises a stopper element with a shape mating with said collection aperture, and a support arm pivoted in said conveyor body and to which the stopper element is attached.

8. The device as in claim 7, including a second delivery nozzle having a delivery aperture facing toward a connection zone of said support arm to said conveyor body.

9. The device as in claim 1, wherein said at least one delivery nozzle is connected to a gas feed unit provided with sterilization devices suitable to sterilize a gas and to feed it to the at least one delivery nozzle.

10. The device as in claim 1, wherein one or more diverters are installed in said conveyor body configured to divert the stream of loose products.

11. The device as in claim 1, in combination with a treatment machine, the treatment machine comprising a treatment chamber in which loose products are treated, said treatment chamber comprising at least one discharge aperture attached to the device.

12. A method for discharging loose products from a treatment machine, comprising: arranging the treatment machine to make said loose products pass through a conveyor body of a discharge device attached with a first end to said treatment machine, providing at least one perimeter wall and providing the treatment machine, in correspondence with a second end opposite the first end, with a bottom wall disposed transversely to the at least one perimeter wall to partly occlude a tubular transit section of the conveyor body, said method providing to discharge said loose products through a collection aperture, selectively openable/closable by an opening/closing member, and provided in said bottom wall, and further comprising emitting, with a delivery nozzle, a stream of gas incident against said bottom wall to determine the discharge, through said collection aperture, at least of the loose products that are deposited on said bottom wall.

* * * * *